(12) United States Patent
Zhang et al.

(10) Patent No.: US 9,474,873 B2
(45) Date of Patent: Oct. 25, 2016

(54) TRAINING DEVICE FOR TREATING SNORING AND APNEA

(71) Applicants: Zhenfang Zhang, Ypsilanti, MI (US); Yuezhuo Zhang, Ypsilanti, MI (US)

(72) Inventors: Zhenfang Zhang, Ypsilanti, MI (US); Yuezhuo Zhang, Ypsilanti, MI (US)

( * ) Notice: Subject to any disclaimer, the term of this patent is extended or adjusted under 35 U.S.C. 154(b) by 393 days.

(21) Appl. No.: 14/298,703

(22) Filed: Jun. 6, 2014

(65) Prior Publication Data

US 2014/0360510 A1    Dec. 11, 2014

Related U.S. Application Data

(60) Provisional application No. 61/831,855, filed on Jun. 6, 2013.

(51) Int. Cl.
*A61M 16/00* (2006.01)
*A61M 16/04* (2006.01)
*A61F 5/56* (2006.01)
*A61M 16/06* (2006.01)

(52) U.S. Cl.
CPC .......... *A61M 16/0078* (2013.01); *A61F 5/566* (2013.01); *A61M 16/049* (2014.02); *A61M 16/0493* (2014.02); *A61M 16/0666* (2013.01)

(58) Field of Classification Search
CPC ..... A61M 16/0078–16/0084; A61M 16/0045; A61M 16/0488–16/0497; A61M 16/06; A61M 16/0666–16/0694; A61M 21/00; A61M 5/56–5/566; A61M 5/08
See application file for complete search history.

(56) References Cited

U.S. PATENT DOCUMENTS

| | | | | |
|---|---|---|---|---|
| 2004/0112379 A1* | 6/2004 | Djupesland | ............ | A61B 5/085 128/203.12 |
| 2011/0218451 A1* | 9/2011 | Lai | ............. | A61F 5/56 600/533 |
| 2011/0315143 A1* | 12/2011 | Frater | ............ | A61M 16/06 128/205.24 |

* cited by examiner

*Primary Examiner* — Rachel Young

(57) ABSTRACT

A training device for treating snoring and apnea is creates positive pressure within a user's nasal passages during exhalation. Exhaling through a breathing tube inflates a primary inflation chamber and a secondary inflation chamber. The secondary inflation chamber is positioned in proximity to the user's nose while inflated, blocking the majority of any nasal exhalations and controlling nasal airflow and pressure.

7 Claims, 5 Drawing Sheets

TRAINING DEVICE FOR TREATING SNORING AND APNEA

The current application claims a priority to the U.S. Provisional Patent application Ser. No. 61/831,855 filed on Jun. 6, 2013.

FIELD OF THE INVENTION

The present invention relates to a device for treating sleep apnea. More particularly, the present invention relates to a breathing training device for generating positive pressure in users' airways to keep the airway open and maintain normal breathing.

BACKGROUND OF THE INVENTION

Sleep apnea is a disease characterized by temporary blocking of breathing during sleeping. This device can be used for obstructive apnea and mixed apnea. In obstructive apnea, ventilating effort is present but no air flow results because of upper airway closure. In mixed apnea, there is initially no ventilating effort, but obstructive sleep apnea pattern becomes evident when ventilator effort resumes. Hypopnea is a temporary decrease in inspiratory airflow that is out of propulsion to individual effort or metabolic needs. The terms sleep apnea and/or sleep disorder breathing may refer to hypopnea. Pursed-lip breathing has been confirmed to have benefit for Chronic Obstructive Pulmonary Disease ("COPD") patient. It has been found that pursed-lip breathing results in a reduction in respiratory rate and increase in tidal volume and an improvement of oxygen saturation. All of the effort contributes to a reduction in patient dyspnea. The pursed-lip breathing could hardly be trained without a device to help the users because when they fall asleep, they do not have conscious effort, thus the patient cannot breathe while the mouth is closed when sleeping.

The CPAP device is a standard method to treat the patients. However, it has its limitations:
- Most patients cannot tolerate the mask and stop using the CPAP machine after a period of time.
- The nose and facial mask leaks are a common issue.
- Nasal congestion and dryness are common complaints.
- A source of power is needed.
- It is bulky and inconvenient when traveling.

Expiratory resistance can provide clinical improvements when using pursed-lip breathing. On the contrary, inspiratory support is not shown to offer clinical benefits in many patients. It would be beneficial to have the pursed-lip training device to allow patients to do so during sleeping.

It is therefore the objective of the present invention to provide a pursed lip training device to allow for creation of positive pressure in constricted airways of a patient suffering from sleep apnea and/or other respiratory diseases. It is another objective of the present invention to provide a multiple-use device that has no mask to wear to treat sleep apnea.

It is a further objective of the present invention to provide a pursed-lip device to treat other diseases such as hypertension or heart failure.

It is another objective of the present invention to provide a mouthpiece with a positive air pressure or reservoir to help the inhalation process.

DETAIL DESCRIPTIONS OF THE INVENTION

Figure 1:
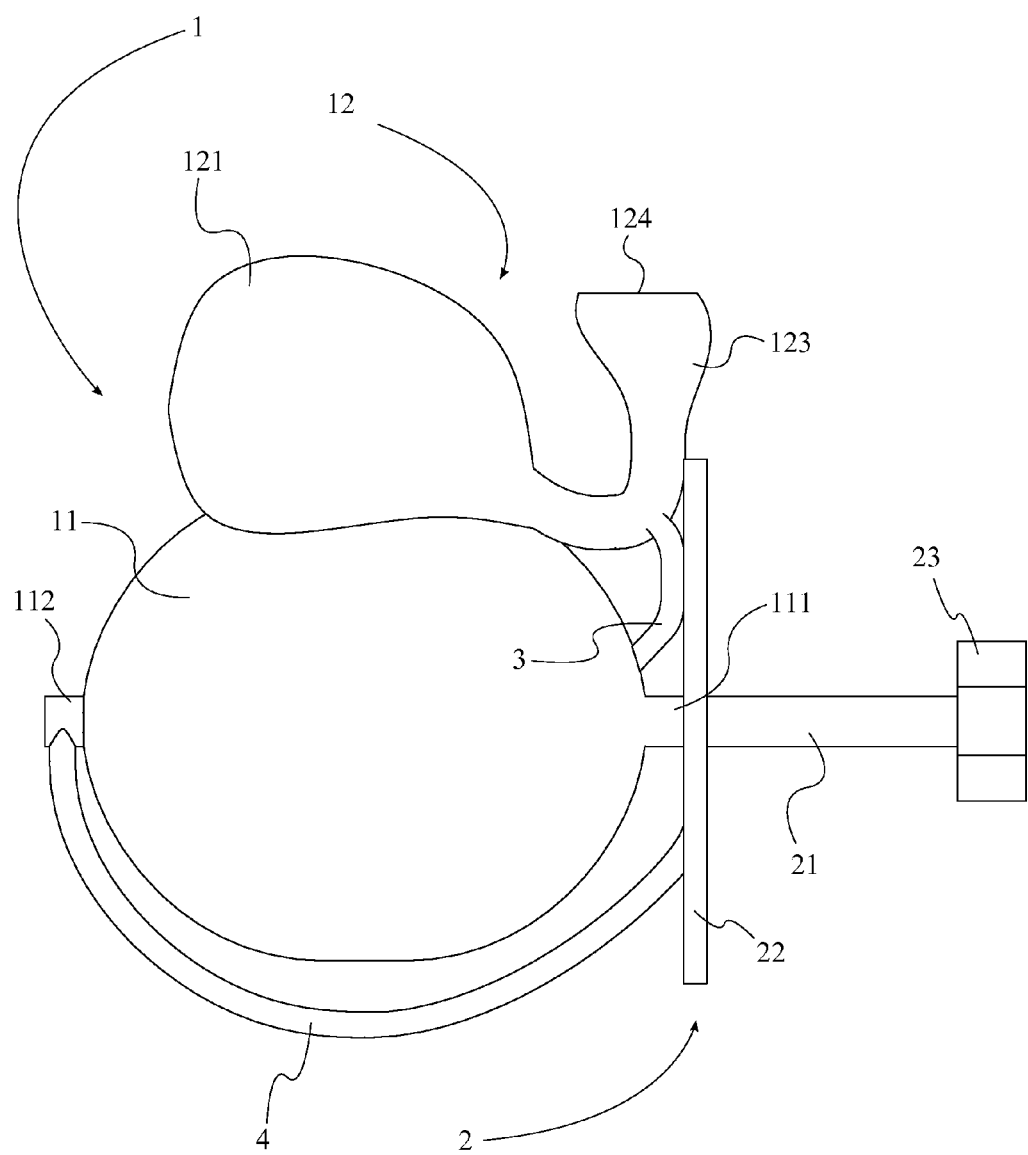
FIG. 1 is a side view of the present invention.

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced without the implementation of some features as they are described. It should be understood that some details have not been described in detail in order to not unnecessarily obscure focus of the invention.

The present invention is a device for treating apnea and snoring which is held between the pursed lips and adjacent to the nose of a user, and which regulates airflow through the oral and nasal passages, particularly by creating positive pressure within the nasal passages during exhalation in order to treat sleep apnea, snoring or other respiratory diseases or conditions. The present invention comprises a mouthpiece 2 and a nasal piece 1, through which oral and nasal airflow, respectively, are regulated. The mouthpiece 2 is held within the mouth between pursed lips, and the nasal piece 1 is connected to the mouthpiece 2, supported adjacent to the user's nostrils. The primary purpose of the present invention is to restrict nasal airflow during exhalation in order to create positive pressure within the user's nasal passages.

The mouthpiece 2 comprises a breathing tube 21 which is positioned within and traverses out of a user's mouth when in use. The user should purse their lips around the breathing tube 21 in order to restrict the path of oral exhalation to only the breathing tube 21.

In the preferred embodiment of the present invention, the nasal piece 1 functions to restrict nasal exhalation through the use of a flexible, inflatable, balloon-like chamber which inflates upon exhalation through either the nose or the mouth, blocking a large portion of the nostrils and thereby restricting airflow out from the nostrils, while deflating upon inhalation in order to allow free air flow. In one embodiment of the present invention, the nasal piece 1 can be secured to the nose by itself with a nasal support member which is connected to and extends from the secondary inflation chamber 12 and matches the inner profile of the nostril. The nasal support member may be similar to the communication channel 3 of the alternate embodiment shown in FIGS. 4-5.

Figure 2:
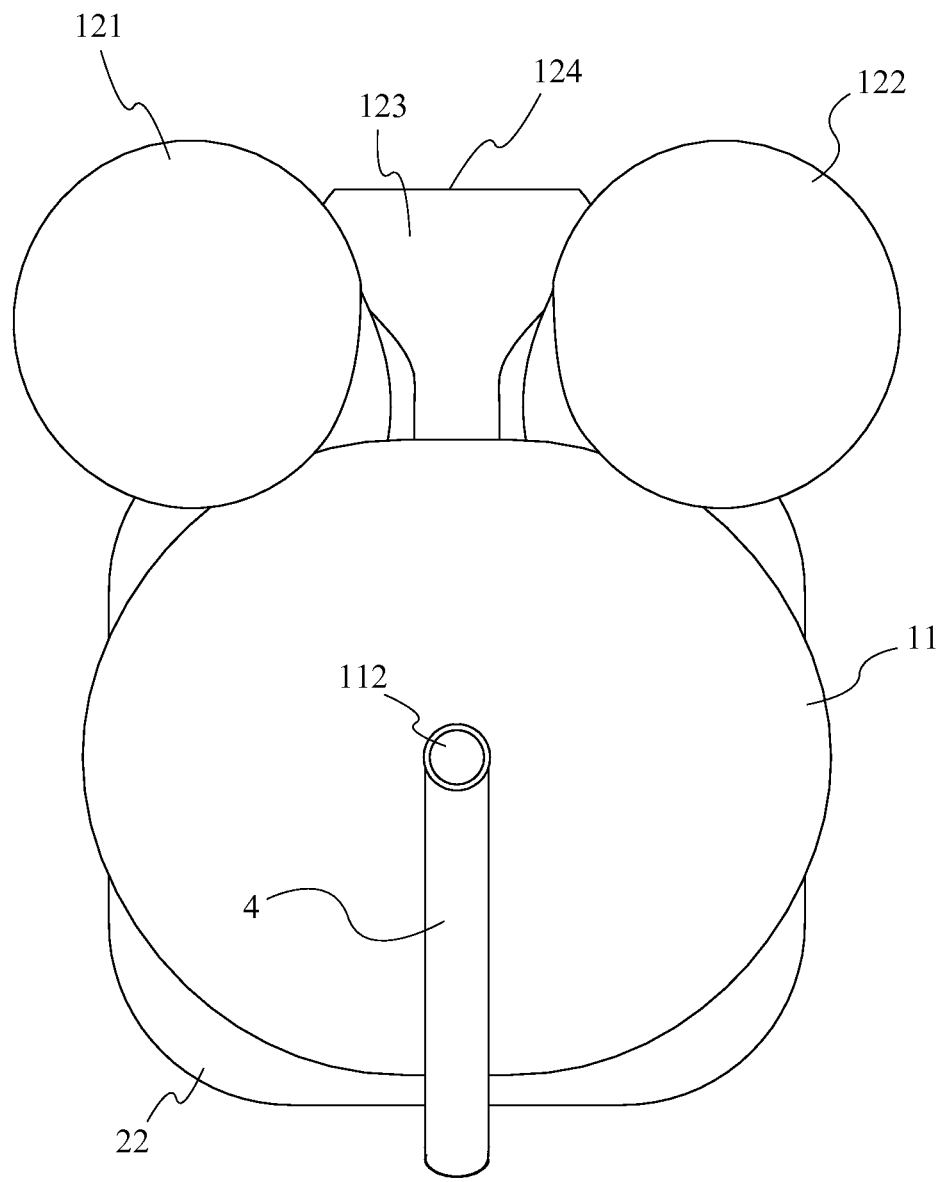
FIG. 2 is a front view of the present invention.
Figure 3:
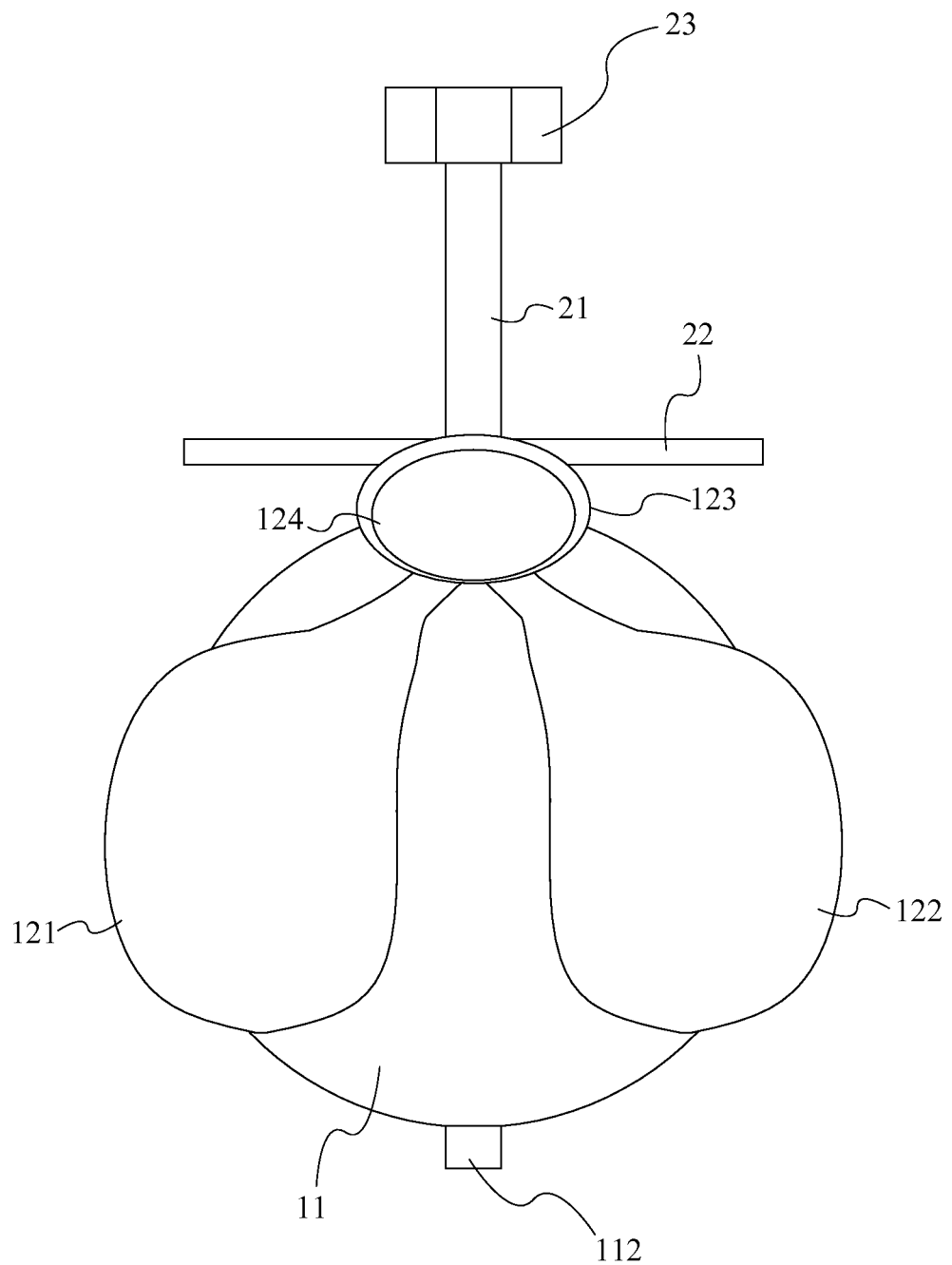
FIG. 3 is a top view of the present invention.

Referring to FIGS. 1-3, in the preferred embodiment, the nasal piece 1 comprises a primary inflation chamber 11 and a secondary inflation chamber 12. The primary inflation chamber 11 comprises a first airflow port 111 and a second airflow port 112, which are openings in the walls of the primary inflation chamber 11 through which the exhaled breath of the user passes. The breathing tube 21 is connected to the first airflow port 111, so that the breathing tube 21 is in fluid communication with the primary inflation chamber 11 through the first port; therefore, orally exhaled breath passes through the breathing tube 21 and into the primary inflation chamber 11 at the first airflow port 111. Exhaled breath additionally exist the primary inflation chamber 11 through the second airflow port 112, which is preferably positioned opposite the first airflow port 111 on the primary inflation chamber 11.

The secondary inflation chamber 12 is connected atop the primary inflation chamber 11, wherein the secondary inflation chamber 12 is positioned in proximity to the user's nostrils when in use and functions as a nasal airflow resistor when inflated by obstructing a large portion of the user's nostrils. In the preferred embodiment of the present invention, the primary inflation chamber 11 and the secondary inflation chamber 12 are in fluid communication. This means that as the user exhales through the breathing tube 21, the primary inflation chamber 11 and the secondary inflation chamber 12 both inflate due to being pressurized from the user's exhalation, thus mostly obstructing the user's nasal passages with the secondary inflation chamber 12 and thereby restricting a significant portion of possible nasal exhalation during oral exhalation. In an alternate embodiment, the primary inflation chamber 11 and the secondary inflation chamber 12 are not in fluid communication, and are separate chambers the walls of which are attached to each other. In this alternate embodiment, the secondary inflation chamber 12 is either a rigid structure which is seated adjacent to and obstructing the user's nasal passages by inflation of the primary inflation chamber 11, or the secondary inflation chamber 12 is inflated solely by an exhalation intake port 124 described hereinafter.

In the preferred embodiment of the present invention, the primary inflation chamber 11 and the secondary inflation chamber 12 are connected by a communication channel 3, wherein air can flow between the primary inflation chamber 11 and the secondary inflation chamber 12 through the communication channel 3. Preferably, the communication channel 3 is a hollow tube, though the communication channel 3 may take other forms which fulfill the function of allowing air to flow between the primary inflation chamber 11 and the secondary inflation chamber 12.

In the preferred embodiment of the present invention, the secondary inflation chamber 12 comprises a first airflow resistor chamber 121, a second airflow resistor chamber 122, and an intake chamber 123. The first airflow resistor chamber 121 and the second airflow resistor chamber 122 are positioned laterally adjacent to each other, and each is positioned to obstruct one nostril. The intake chamber 123 comprises an exhalation intake port 124, wherein the exhalation intake port 124 receives nasal exhalation from the user while the present invention is in use if the user exhales through their nose. The exhalation intake port 124 is oriented away from the primary inflation chamber 11, wherein the exhalation intake port 124 is positioned adjacent to and oriented toward the user's nose while in use, thereby being able to receive any nasal exhalation, which functions to inflate the secondary inflation chamber 12 in order to obstruct the user's nostrils. The first airflow resistor chamber 121, the second airflow resistor chamber 122, and the intake chamber 123 are in fluid communication, wherein nasal exhalation received through the exhalation intake port 124 inflates the first airflow resistor chamber 121 and the second airflow resistor chamber 122.

Figure 4:
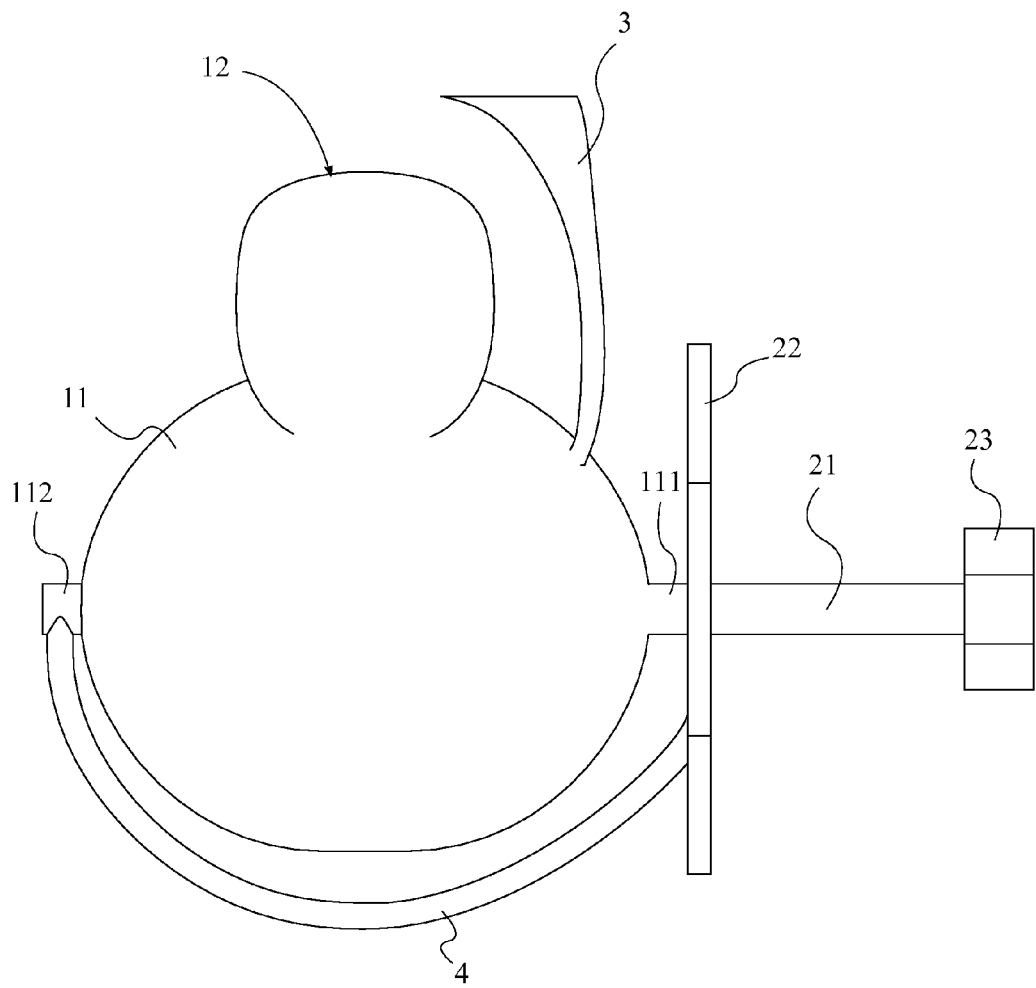
FIG. 4 is a side view of an alternate embodiment of the present invention.
Figure 5:
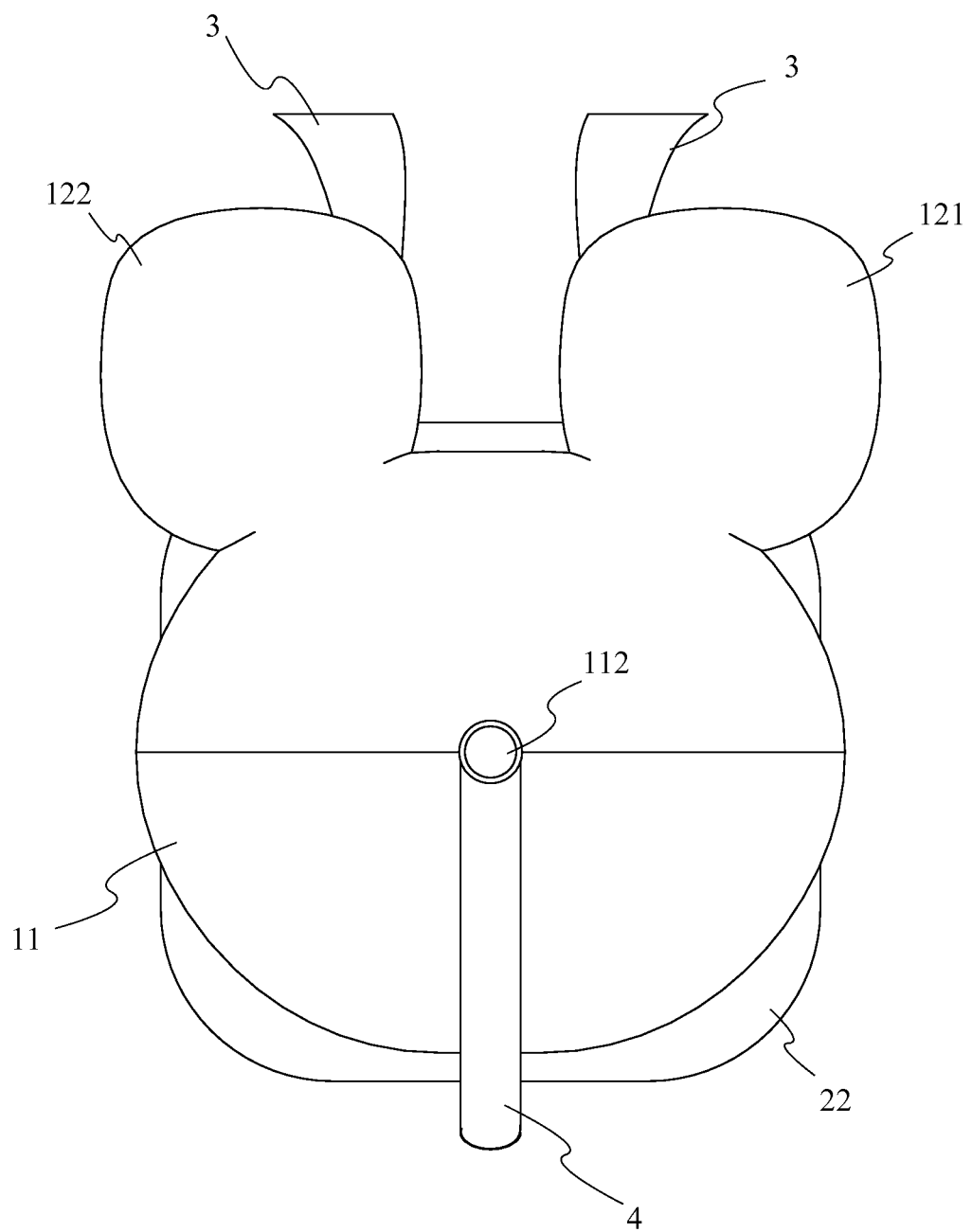
FIG. 5 is a front view of an alternate embodiment of the present invention.

In an alternate embodiment of the present invention shown in FIGS. 4-5, the secondary inflation chamber 12 does not comprise an intake chamber 123. Nasal exhalations are received by a nasal communication channel 3 positioned within the user's nose and is connected to and provides fluid communication to the primary inflation chamber 11, so that nasal exhalation gases function to add pressure to the primary inflation chamber 11 and subsequently the secondary inflation chamber 12. In this alternate embodiment, the first airflow resistor chamber 121 and the second airflow resistor chamber 122 are each connected directly to the primary inflation chamber 11 adjacent to each other, forming a shape with the primary inflation chamber 11 and the secondary inflation chamber 12 resembling rabbit ears.

In the preferred embodiment of the present invention, the mouthpiece 2 further comprises a mouth guard 22 and an interior mouth piece 23. The mouth guard 22 and the interior mouth piece 23 are connected around the breathing tube 21. The mouth guard 22 is positioned adjacent to the primary inflation chamber 11. The mouth guard 22 and the interior mouth piece 23 are separated from each other along the breathing tube 21, so that the mouth guard 22 is positioned on the exterior of the user's mouth while the present invention is in use, and the interior mouth piece 23 is positioned within the user's mouth while in use. The interior mouth piece 23 may be of any configuration which facilitates the user's ability to hold the present invention in their mouth in the proper orientation. In the preferred embodiment, the interior mouth piece 23 is preferably a piece of rubber which the user clamps between their upper and lower teeth. Alternatively, the interior mouth piece 23 may be formed appropriately to be placed behind the upper and lower teeth in order to prevent the interior mouth piece 23 from moving back and forth laterally within the mouth.

Additionally, a support member 4 is connected between the mouthpiece 2 and the primary inflation chamber 11, wherein the support member 4 functions to support the primary inflation chamber 11 in place. Preferably, the support member 4 is connected to the mouthpiece 2 at the breathing tube 21, though the support member 4 may be connected to other components of the mouthpiece 2 such as, but not limited to, the mouth guard 22.

Although the invention has been explained in relation to its preferred embodiment, it is to be understood that many other possible modifications and variations can be made without departing from the spirit and scope of the invention as hereinafter claimed.

What is claimed is:

1. A training device for treating snoring and apnea comprises:
    a breathing tube, wherein the breathing tube is positioned within and traverses out of a user's mouth when in use;
    a primary inflation chamber comprising a first airflow port and a second airflow port;
    a secondary inflation chamber;
    the breathing tube being connected to the first airflow port, wherein the breathing tube is in fluid communication with the primary inflation chamber through the first port;
    the secondary inflation chamber being connected atop the primary inflation chamber,
    wherein the secondary inflation chamber is positioned in proximity to the user's nostrils when in use and functions as a nasal airflow resistor when inflated;
    wherein obstruction of the user's nostrils functions to create positive pressure within the user's nasal passages; and
    the primary inflation chamber and the secondary inflation channel being in fluid communication with each other.

2. The training device for treating snoring and apnea as claimed in claim 1 comprises:
    a mouth guard and an interior mouth piece;
    the mouth guard and the interior mouth piece being connected around the breathing tube;
    the mouth guard being positioned adjacent to the primary inflation chamber; and
    the mouth guard and the interior mouth piece being separated from each other along the breathing tube, wherein the mouth guard is positioned on the exterior of the user's mouth while in use and the interior mouth piece is positioned within the user's mouth while in use.

3. The training device for treating snoring and apnea as claimed in claim 1 comprises:
the primary inflation chamber and the secondary inflation chamber being connected by a communication channel, wherein air can flow between the primary inflation chamber and the secondary inflation chamber through the communication channel.

4. The training device for treating snoring and apnea as claimed in claim 3, wherein the communication channel is a tube.

5. The training device for treating snoring and apnea as claimed in claim 1 comprises:
the secondary inflation chamber comprises a first airflow resistor chamber, a second airflow resistor chamber, and an intake chamber;
the intake chamber comprises an exhalation intake port, wherein the exhalation intake port receives nasal exhalation from the user when in use;
the exhalation intake port being oriented away from the primary inflation chamber, wherein the exhalation intake port is positioned adjacent to and oriented toward the user's nose while in use; and
the first airflow resistor chamber, the second airflow resistor chamber, and the intake chamber being in fluid communication with each other, wherein nasal exhalation received through the exhalation intake port inflates the first airflow resistor chamber and the second airflow resistor chamber.

6. The training device for treating snoring and apnea as claimed in claim 1 comprises:
a support member being connected between the breathing tube and the primary inflation chamber, wherein the support member functions to support the primary inflation chamber in place.

7. The training device for treating snoring and apnea as claimed in claim 1 comprises:
a nasal support member being connected to and extending from the secondary inflation chamber, wherein the nasal support member is adapted to match the inner profile of the nostril and facilitates being secured within the nostril.

\* \* \* \* \*